United States Patent [19]

Pfenninger

[11] 4,235,907
[45] Nov. 25, 1980

[54] SUBSTITUTED-9H-PYRROLO[3,4-b]QUINO-LIN-9-ONES AND TREATMENT OF ALLERGIC CONDITIONS WITH THEM

[75] Inventor: Emil Pfenninger, Allschwil, Switzerland

[73] Assignee: Sandoz Ltd., Basel, Switzerland

[21] Appl. No.: 27,893

[22] Filed: Apr. 6, 1979

Related U.S. Application Data

[63] Continuation of Ser. No. 842,200, Oct. 14, 1977, abandoned.

[30] Foreign Application Priority Data

Oct. 15, 1976 [CH] Switzerland ............... 13086/76

[51] Int. Cl.³ .................... A61K 31/47; C07D 471/04
[52] U.S. Cl. ...................................... 424/258; 546/84
[58] Field of Search ............................ 546/84; 424/258

[56] References Cited

FOREIGN PATENT DOCUMENTS 2023514 12/1971 Fed. Rep. of Germany .
2521544 12/1976 Fed. Rep. of Germany .

OTHER PUBLICATIONS

Madhav, et al., Chemical Abstracts, vol. 79, 53199j (1973).

Primary Examiner—Donald G. Daus
Assistant Examiner—Diana G. Rivers
Attorney, Agent, or Firm—Gerald D. Sharkin; Robert S. Honor; Timothy G. Rothwell

[57] ABSTRACT

This invention provides compounds of formula

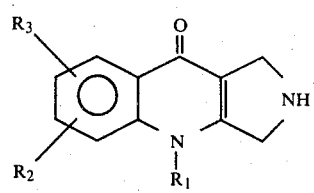

wherein
$R_1$ is hydrogen, alkyl, alkenyl or alkynyl, the multiple bond of which is not adjacent to the nitrogen atom,
$R_2$ is, for example, hydrogen, alkyl, alkoxy, hydroxy or halogen, and
$R_3$ is hydrogen, halogen, hydroxyl, alkyl or alkoxy, useful, for example, in the treatment of allergic asthma.

36 Claims, No Drawings

SUBSTITUTED-9H-PYRROLO[3,4-B]QUINOLIN-9-ONES AND TREATMENT OF ALLERGIC CONDITIONS WITH THEM

This is a continuation of application Ser. No. 842,200 filed Oct. 14, 1977, now abandoned.

The present invention relates to 1,2,3,4-tetrahydro-9H-pyrrolo[3,4-b]quinolin-9-one derivatives.

More particularly, the present invention provides compounds of formula I,

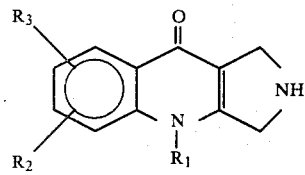

wherein
- $R_1$ is hydrogen, alkyl of 1 to 4 carbon atoms, alkenyl or alkynyl, each of 3 to 5 carbon atoms, the multiple bond of which is not adjacent to the nitrogen atom,
- $R_2$ is hydrogen, alkyl or alkoxy, each of 1 to 8 carbon atoms, hydroxyl, fluorine, chlorine, bromine, trifluoromethyl, carboxyl or $-NR_4R_5$,
- $R_3$ is hydrogen, fluorine, chlorine, bromine, hydroxyl, alkyl or alkoxy, each of 1 to 8 carbon atoms,
- $R_4$ is hydrogen, alkyl of 1 to 4 carbon atoms, phenyl or $-SO_2R_6$,
- $R_5$ is hydrogen or alkyl of 1 to 4 carbon atoms and
- $R_6$ is alkyl of 1 to 4 carbon atoms, phenyl or phenyl monosubstituted by alkyl or alkoxy, each of 1 to 4 carbon atoms, fluorine, chlorine or bromine.

When $R_1$ is alkyl, this is preferably methyl. $R_1$ is preferably hydrogen or methyl. When $R_1$ is alkenyl of 3 to 5 carbon atoms, this may, for example, be propenyl. $R_1$ may also be alkynyl of 3 to 5 carbon atoms, for example, butynyl.

$R_2$ is preferably chlorine or trifluoromethyl. $R_2$ can also be fluorine or bromine. $R_2$ may be alkyl of 1 to 8 carbon atoms, suitably of 1 to 6 carbon atoms or of 1 to 3 carbon atoms, for example, methyl, propyl, hexyl or octyl. $R_2$ may be alkoxy of 1 to 8 carbon atoms, suitably of 1 to 6 carbon atoms or of 1 to 3 carbon atoms, for example, methoxy, propoxy, hexyloxy or octyloxy. In one group of compounds, $R_2$ is hydroxy. In a second group of compounds, $R_2$ is carboxyl. When $R_2$ is $-NR_4R_5$, $R_4$ and $R_5$ may each be alkyl of 1 to 4 carbon atoms. $R_4$ may also be phenyl. When $R_4$ is $-SO_2R_6$, $R_6$ may be alkyl of 1 to 4 carbon atoms. $R_6$ may also be phenyl or phenyl monosubstituted by alkyl or alkoxy, each of 1 to 4 carbon atoms, fluorine or chlorine.

$R_3$ is preferably hydrogen. $R_3$ may be fluorine, chlorine or bromine. In one group of compounds, $R_3$ is hydroxy. $R_3$ may be alkyl of 1 to 8 carbon atoms, suitably of 1 to 6 carbon atoms or of 1 to 3 carbon atoms, for example, methyl, propyl, hexyl or octyl. $R_3$ may be alkoxy of 1 to 8 carbon atoms, suitably of 1 to 6 carbon atoms or of 1 to 3 carbon atoms, for example, methoxy, propoxy, hexyloxy or octyloxy.

In one group of compounds, $R_1$ is alkyl of 1 to 4 carbon atoms, $R_2$ is fluorine, chlorine, bromine or trifluoromethyl and $R_3$ is hydrogen.

The invention further provides a process for the production of a compound of formula I, comprising hydrolysing a compound of formula II,

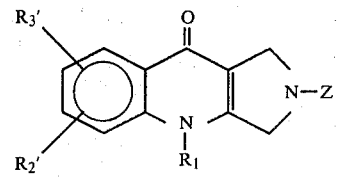

wherein
- $R_1$ is as previously defined,
- $R'_2$ is hydrogen, alkyl or alkoxy, each of 1 to 8 carbon atoms, hydroxyl, fluorine, chlorine, bromine, trifluoromethyl, $-COOR_7$, $-OOCR_8$ or $-NR'_4R_5$,
- $R'_3$ is hydrogen, alkyl or alkoxy, each of 1 to 8 carbon atoms, hydroxyl, fluorine, chlorine, bromine or $-OOCR_8$,
- $R'_4$ is hydrogen, alkyl of 1 to 4 carbon atoms, phenyl, $-SO_2R_6$ or $-Z$,
- $R_7$ is alkyl of 1 to 4 carbon atoms,
- $R_8$ is hydrogen, alkyl of 1 to 4 carbon atoms, phenyl or p-nitrophenyl,
- $Z$ is $-CO-Y$,
- $Y$ is hydrogen, alkyl or alkoxy, each of 1 to 4 carbon atoms, phenyl, p-nitrophenyl or phenoxy,
- and $R_5$ and $R_6$ are as previously defined.

The conversion of the compounds of formula II to the compounds of formula I can be effected by known methods for the hydrolysis of carboxylic acid amides or carbamates to secondary amines. The hydrolysis can be effected in an acid medium, e.g. with HBr in glacial acetic acid, or in an alkaline medium, e.g. with an alkali hydroxide such as NaOH or KOH or with $Ba(OH)_2$ in an aqueous alcohol.

The hydrolysis is preferably effected at the reflux temperature of the reaction mixture. The $R_8COO-$, $-COOR_7$ and/or $NR_5Z$ groups which may be present are simultaneously converted to hydroxyl, free carboxyl or $-NHR_5$ groups, respectively.

The resulting compounds of formula I may be isolated and purified using conventional techniques.

Free base forms of the compounds of formula I may be converted into acid addition salt forms and vice versa in conventional manner.

The starting materials of formula II may be produced as follows:

(a) Compounds of formula IIa,

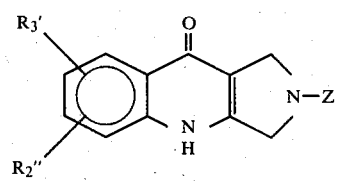

wherein
- $R'_3$ and $Z$ are as previously defined, and
- $R''_2$ has the same significance as $R'_2$ with the exception of $-NH_2$, may, for example, be obtained by cyclisation of compounds of formula III,

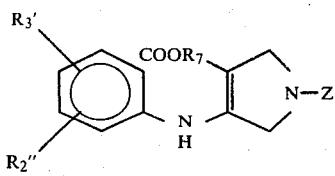

III wherein $R'_3$, $R''_2$, $R_7$ and Z are as previously defined.

The cyclisation can be effected according to known methods (Conrad-Limpach cyclisation) by heating to temperatures of between ca. 220° and ca. 300° in an inert solvent such as diphenyl ether.

The compounds of formula III can be produced by condensing compounds of formula IV,

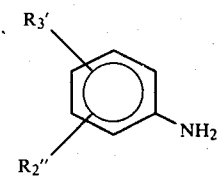

IV wherein $R'_3$ and $R''_2$ are as previously defined, with compounds of formula V,

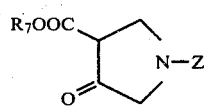

V wherein $R_7$ and Z are as previously defined.

The condensation can be effected according to known methods for the condensation of anilines with β-keto esters, for example, by boiling in $CCl_4$ or ethanol, optionally in the presence of an acid catalyst such as hydrochloric acid or formic acid or acid salts, e.g. $MgSO_4$ or $CdSO_4$.

The compounds of formula IV and V are either known or may be produced by known methods.

(b) Compounds of formula IIb,

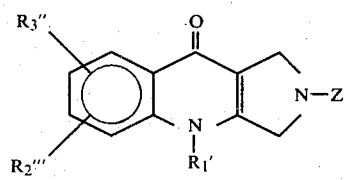

IIb wherein $R'_1$ has the same significance as $R_1$ with the exception of hydrogen, $R'''_2$ is hydrogen, alkyl or alkoxy, each of 1 to 8 carbon atoms, fluorine, chlorine, bromine, trifluoromethyl, —$COOR_7$, —$OOCR_8$ or —$NR''_4R'_5$, $R''_3$ is hydrogen, alkyl or alkoxy, each of 1 to 8 carbon atoms, fluorine, chlorine, bromine or —$OOCR_8$, $R''_4$ is alkyl of 1 to 4 carbon atoms, phenyl or Z, $R'_5$ is alkyl of 1 to 4 carbon atoms and $R_7$, $R_8$ and Z are as previously defined, are produced by alkylating compounds of formula VI,

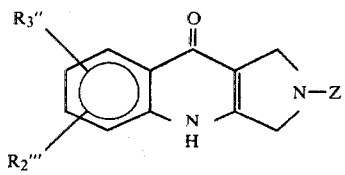

VI wherein $R'''_2$, $R''_3$ and Z are as previously defined.

The N-alkylation can be effected according to known methods, for example, by producing the Na salt with sodium alcoholate in an alcohol and reaction of the salt with an alkyl halide $R'_1X$ (wherein X is Cl, Br or I) in an inert solvent such as dimethyl formamide or hexamethyl phosphoric triamide or by adding sodium hydride to the base of formula VI and subsequently $R'_1X$ in a solvent such as dimethyl formamide or hexamethyl phosphoric triamide.

(c) Compounds of formula IIc,

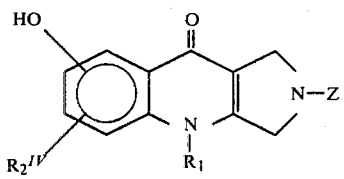

IIc wherein $R_1$ and Z are as previously defined and $R_2^{IV}$ is hydrogen, alkyl of 1 to 8 carbon atoms, hydroxyl, fluorine, chlorine, bromine, trifluoromethyl, —$COOR_7$, —$OOCR_8$ or —$NR'_4R_5$, can be obtained by subjecting a compound of formula VII,

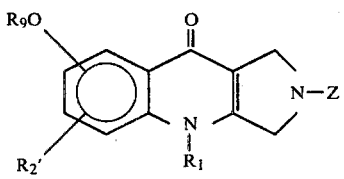

VII wherein $R_1$, $R'_2$ and Z are as previously defined and $R_9$ is alkyl of 1 to 4 carbon atoms or benzyl, to ether splitting.

The ether splitting can be effected according to known methods, for example, with Lewis acids, such as $BBr_3$ or $BCl_3$, in an inert solvent such as methylene chloride, at temperatures of approximately −30° C. to room temperature.

(d) Compounds of formula IId,

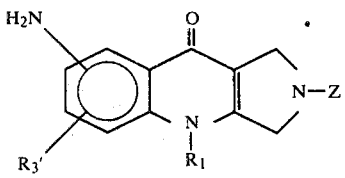

IId wherein $R_1$, $R'_3$ and Z are as previously defined, can, for example, be prepared by reducing the nitro group in a compound of formula VIII,

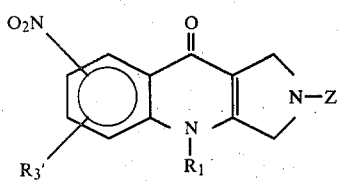

wherein $R_1$, $R'_3$ and Z are as previously defined, to an amino group.

The reaction can be effected according to known methods for reducing aromatic nitro compounds to their corresponding amino derivatives. For example, the compounds of formula VIII can be treated with reducing agents such as $TiCl_3$ or $SnCl_2$ in acidic aqueous solution at temperatures of between room temperature and ca. 60° C. A hydrogenolytic reduction of the nitro group, e.g. with hydrogen in the presence of a catalyst such as Raney nickel or palladium on charcoal in an inert solvent such as ethanol or dimethyl formamide at from room temperature to ca. 50° C., can be used for the production of compounds IId. In this latter case, halogen atoms ($R_3$) or benzyl groups ($R_3$) may be split off and alkenyl or alkynyl groups ($R_1$) may be converted into alkyl groups.

The starting materials of formula VIII can be prepared in manner analogous to processes (a) and (b).

(e) Compounds of formula IIe,

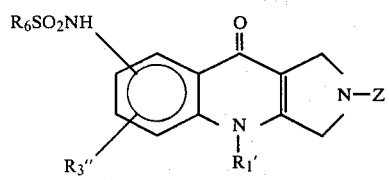

wherein $R'_1$, $R''_3$, $R_6$ and Z are as previously defined, can be prepared by acylating a compound of formula IX,

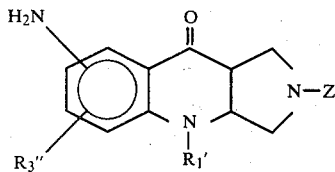

wherein $R'_1$, $R''_3$ and Z are as previously defined, with a compound of formula X, $R_6SO_2M$      X wherein $R_6$ is as previously defined and M is halogen.

The acylation can be effected according to known methods, for example, in the presence of a base such as pyridine, in an inert solvent such as methylene chloride, or according to a Schotten-Baumann reaction.

Processes (c) and (d) for the production of the starting materials of formula II can also be employed for the production of the final products of formula I. Thus, the compounds of formula VII and VIII, wherein Z signifies hydrogen, may respectively be converted into compounds of formula IIc and IId (Z=H) according to process (c) and (d), respectively.

Insofar as the production of starting materials is not described, these are either known or may be produced in accordance with known processes, or in manner analogous to the processes described herein, or to known processes.

In the following non-limitative Examples, all temperatures are indicated in degrees Celsius.

EXAMPLE 1

1,2,3,4-Tetrahydro-4-methyl-9H-pyrrolo[3,4-b]quinolin-9-one

A mixture of 10 g of 2-benzoyl-1,2,3,4-tetrahydro-4-methyl-9H-pyrrolo[3,4-b]quinolin-9-one, 10 g of potassium hydroxide, 10 ml of water and 100 ml of ethanol is heated at reflux for 17 hours, cooled, diluted with 50 ml each of ether and water and filtered. The recrystallisation of the residue from methanol and ether yields 1,2,3,4-tetrahydro-4-methyl-9H-pyrrolo[3,4-b]quinolin-9-one. M.P. 209°–213° (decomposition).

The 2-benzoyl-1,2,3,4-tetrahydro-4-methyl-9H-pyrrolo[3,4-b]quinolin-9-one used as starting material can be prepared as follows:

(a)

3-Anilino-1-benzoyl-2,5-dihydro-1H-pyrrol-4-carboxylic acid ethyl ester

A mixture of 100 g of 1-benzoyl-3-oxopyrrolidin-4-carboxylic acid ethyl ester, 42 ml of aniline and 23 ml of formic acid in 1.2 liters of ethanol is heated to reflux for 15 hours, concentrated by evaporation and the residue is crystallised from the ether/methylene chloride. 3-Anilino-1-benzoyl-2,5-dihydro-1H-pyrrol-4-carboxylic acid ethyl ester is obtained. M.P. 149°–151°.

(b)

2-Benzoyl-1,2,3,4-tetrahydro-9H-pyrrolo[3,4-b]-quinolin-9-one 50 g of 3-anilino-1-benzoyl-2,5-dihydro-1H-pyrrol-4-carboxylic acid ethyl ester are heated at reflux in 500 ml of diphenyl ether for 1.5 hours, the resulting ethanol being continuously distilled off. Upon cooling, the resulting precipitate is filtered by suction, washed with ether and dried. 2-Benzoyl-1,2,3,4-tetrahydro-9H-pyrrolo[3,4-b]-quinolin-9-one is obtained. M.P. 275°.

(c)

2-Benzoyl-1,2,3,4-tetrahydro-4-methyl-9H-pyrrolo-[3,4-b]quinolin-9-one 14.51 g (50 mmol) of the 2-benzoyl-1,2,3,4-tetrahydro-9H-pyrrolo[3,4-b]quinolin-9-one are dissolved in 50 ml of a 1 N solution of sodium methylate in absolute methanol, the solution concentrated by evaporation, the residue taken up in 150 ml of dimethyl formamide and 3.15 ml of methyl iodide are added. After stirring for 4 hours at room temperature, appoximately 100 ml of water are added to the mixture, filtration is effected and the residue is washed with water and dried. The 2-benzoyl-1,2,3,4-tetrahydro-4-methyl-9H-pyrrolo-[3,4-b]quinolin-9-one used in Example 1 is obtained. M.P. 285° (decomposition).

The following compounds can be prepared in manner analogous to that of Example 1, using appropriate starting materials in approximately equivalent amounts.

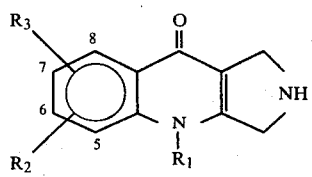

| Ex. No. | R₁ | R₂ | R₃ | M.P. (°C.) | | |
|---|---|---|---|---|---|---|
| 2 | H | H | H | 225°-9° | | (+ ½ H₂O) |
| 3 | H | 7-OCH₃ | H | 280° | Decomp. | (+ ½ H₂O) |
| 4 | CH₃ | 7-Cl | H | 259°-62° | Decomp. | |
| 5 | CH₃ | 7-OCH₃ | H | 166°-8° | Decomp. | (Hydrogenfumarate) |
| 6 | H | 5-CH₃ | H | 286°-8° | Decomp. | |
| 7 | H | 5-F | H | >300° | | (Hydrochloride-hemihydrate) |
| 8 | H | 7-Cl | H | >300° | | (Hydrochloride) |
| 9 | H | 5-CH₃ | 7-Cl | 230° | Decomp. | (Hydrochloride) |
| 10 | H | 5-CH₃ | 7-CH₃ | >300° | | (Hydrochloride) |
| 11 | H | 5-CH₃ | 6-CH₃ | >300° | | (Hydrochloride-dihydrate) |
| 12 | H | 7-C₄H₉ | H | >300° | | (Hydrochloride-hydrate) |
| 13 | H | 5-C₃H₇O | H | 246°-8° | Decomp. | (Hydrochloride-hydrate) |
| 14 | H | 7-C₆H₁₃O | H | 290°-5° | Decomp. | (Hydrochloride) |
| 15 | H | 5-CH₃O | 8-CH₃O | >300° | | (Hydrochloride-hydrate) |
| 16 | CH₂—CH=CH₂ | 5-CH₃ | 7-CH₃ | 135°-8° | Decomp. | |
| 17 | H | 5-CH₃O | 8-CH₃ | >300° | | (Hydrochloride) |
| 18 | H | 6-CF₃ | 7-Cl | >260° | | (Hydrochloride) |
| 19 | C₂H₅ | H | H | 114°-8° | | |
| 20 | H | 5-Cl | 7-Cl | >300° | | (Hydrochloride) |
| 21 | H | 5-CF₃ | H | >270° | | (Hydrochloride) |
| 22 | H | 7-(CH₃)₂N— | H | 224°-30° | Decomp. | (Dihydrochloride-dihydrate) |
| 23 | H | 7-OH | H | >300° | | |
| 24 | CH₃ | 7-NH₂ | H | >300° | | (Hydrate) |
| 25 | —(CH₂)₂—C≡CH | 5-C₃H₇ | 7-C₂H₅ | | | |
| 26 | CH₃ | 7-Br | 5-C₂H₅O | | | |
| 27 | CH₃ | 5-COOH | H | | | |
| 28 | H | H<br>    |<br>6-N—SO₂C₃H₇ | 5-CH₃ | | | |
| 29 | H | H<br>    |<br>7-N—SO₂—⟨O⟩—F | 5-CH₃O | | | |
| 30 | CH₃ | 5-C₄H₉O | 7-F | | | |
| 31 | C₂H₅ | 5-C₇H₁₅ | 7-Br | | | |
| 32 | C₄H₉ | H | 6-OH | | | |
| 33 | H | H<br>    |<br>7-NPh | 5-C₃H₇ | | | |

The compounds of formula I possess pharmacological activity. In particular, the compounds possess disodium chromoglycate (DSCG)-like activity, and are therefore useful in the treatment and prophylaxis of allergic conditions, such as allergic asthma, exercise-induced asthma and allergic gastro-intestinal disorders, as indicated in the passive cutaneous anaphylaxis (PCA) test in the rat.

The method employed is based on those described by Mota (1), Stotland and Share (2) and Perper et al. (3). Female rats (180–200 g) are sensitized by subcutaneous administration of 1 mg of ovalbumin (Fluka No. 05430) and 200 mg of albumin hydroxide gel (Merck No. 1088), dissolved in 1 ml of 0.9% saline, and intraperitoneal administration of 0.5 ml of Haemophilus pertussis vaccine (Schweizerisches Serum- and Impfinstitut, Bern, No. 115,325; 4×10 organism/ml). Fourteen days later, the animals are exsanguinated, the blood centrifuged and the serum (anti-serum) collected and deep frozen.
(1) Mota, I., Immunology 7, 681 (1964).
(2) Stotland, M. and Share, N. N., Can. J. Physiol. Pharmacol. 52, 1114 (1974).
(3) Perper, R. J., Oronsky, A. L. and Blancuzzi, V., J. Allergy Clin. Immunol. 53, 66 (1974).

The anti-serum is injected intradermally (0.1 ml of a 1:100 to 1:200 dilution per injection site) at three sites on the backs of untreated, female rats. Twenty-four hours later (intravenous testing) or forty-eight hours later (oral testing), the rats receive either solvent or the test compound (2 ml/kg i.v. 0.1 to 3.2 mg/kg i.v. or 5 ml/kg p.o. 1 to 32 mg/kg p.o.) followed one minute (intravenous testing), or 7.5 or 15 minutes (oral testing) later by the intradermal injection of histamine (8 μg in 0.05 ml of 0.9% saline) and serotonin (0.5 μg in 0.05 ml of 0.9% saline) at two further sites. Immediately afterwards, the animals receive an intravenous injection of 1 ml of a 0.9% saline solution containing 5 mg of ovalbumin (twice crystallised) and 2.5 mg of Evans blue dye. The ovalbumin, histamine and serotonin elicit a cutaneous anaphylactic/anaphylactoid reaction, the intensity of which is proportional to the distance to which the dye diffuses into the tissue surrounding the seven sensitisation sites. Thirty minutes later, the rats are killed by CO₂ inhalation and the diameter in mm of the blue spot at each anti-serum, histamine and serotonin injection site measured. The drug dose decreasing the diameter of the blue area by 50% compared with solvent pretreated control rats (ED50), is obtained from the regression line. The dose-effect correlation is treated for statistical significance.

The DSCG-like activity, in particular histamine release inhibitor activity, can be confirmed by inhibition of histamine release in the passive peritoneal anaphylaxis test in the rat.

Rats are passively sensitised by intraperitoneal injection of 3 ml of 1:2 to 1:10 diluted rat anti-ovalbumin serum. Twenty-four hours later, the rats are treated intravenously (0.1 to 3.2 mg/kg i.v.) with the test compound. Immediately after intravenous application, the anaphylactic reaction is elicited by intravenous administration of 1 ml of 0.5% ovalbumin, immediately followed by 5 ml of HBSS (Hank's balanced salt solution) intraperitoneally. Five minutes later, the animals are decapitated and the peritoneal fluid collected and kept in an ice bath. After centrifugation for 5 minutes (350 g) at 4° C., the histamine content of the supernatant liquid is estimated fluorophotometrically (4). The effects of the test compounds are expressed as percentage changes in histamine release compared with controls.

(4) Kusner, E. J. and Herzig, D. J., In: Advances in Automated Analysis, vol. II, Thurman Associates, Maimi (1971).

For the above-mentioned use, the dosage will, of course, vary depending on the compound employed, mode of administration and therapy desired. However, in general, satisfactory results are obtained when administered at a daily dosage of from about 0.1 to about 20 mg/kg of animal body weight, conveniently given in divided doses 2 to 4 times a day or in sustained release form. For the larger mammal, the total daily dosage is in the range of from about 0.5 to about 100 mg, and dosage forms suitable for oral administration comprise from about 0.1 to about 50 mg of the compounds admixed with a solid or liquid pharmaceutical carrier or diluent.

What is claimed is:

1. A compound of the formula

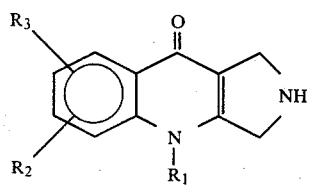

wherein
$R_1$ is hydrogen, alkyl of 1 to 4 carbon atoms, alkenyl or alkynyl, each of 3 to 5 carbon atoms, the multiple bond of which is not adjacent to the nitrogen atom,
$R_2$ is hydrogen, alkyl or alkoxy, each of 1 to 8 carbon atoms, hydroxyl, fluorine, chlorine, bromine, trifluoromethyl, carboxyl or —$NR_4R_5$,
$R_3$ is hydrogen, fluorine, chlorine, bromine, hydroxyl, alkyl or alkoxy, each of 1 to 8 carbon atoms,
$R_4$ is hydrogen, alkyl of 1 to 4 carbon atoms, phenyl or —$SO_2R_6$,
$R_5$ is hydrogen or alkyl of 1 to 4 carbon atoms and
$R_6$ is alkyl of 1 to 4 carbon atoms, phenyl or phenyl monosubstituted by alkyl or alkoxy, each of 1 to 4 carbon atoms, fluorine, chlorine or bromine,
in the form of the free base or in the form of a pharmaceutically acceptable acid addition salt thereof.

2. 1,2,3,4-Tetrahydro-5-trifluoromethyl-9H-pyrrolo[3,4-b]quinolin-9-one.

3. 7-Chloro-1,2,3,4-tetrahydro-4-methyl-9H-pyrrolo[3,4-b]quinolin-9-one.

4. A pharmaceutical composition for use in preventing or treating allergic conditions which comprises an anti-allergic effective amount of a compound according to claim 1 in association with a pharmaceutical carrier or diluent.

5. A method of preventing or treating allergic conditions which comprises administering to an animal in need of such treatment an effective amount of a compound of claim 1.

6. A compound of the formula

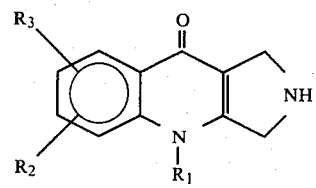

wherein
$R_1$ is hydrogen, alkyl of 1 to 4 carbon atoms, alkenyl or alkynyl, each of 3 to 5 carbon atoms, the multiple bond of which is not adjacent to the nitrogen atom,
$R_2$ is alkyl or alkoxy, each of 1 to 8 carbon atoms, hydroxyl, fluorine, chlorine, bromine, trifluoromethyl, carboxyl or —$NR_4R_5$,
$R_3$ is hydrogen, fluorine, chlorine, bromine, hydroxyl, alkyl or alkoxy, each of 1 to 8 carbon atoms,
$R_4$ is hydrogen, alkyl of 1 to 4 carbon atoms, phenyl or —$SO_2R_6$,
$R_5$ is hydrogen or alkyl of 1 to 4 carbon atoms, and
$R_6$ is alkyl of 1 to 4 carbon atoms, phenyl or phenyl monosubstituted by alkyl or alkoxy, each of 1 to 4 carbon atoms, fluorine, chlorine or bromine,
in the form of the free base or in the form of a pharmaceutically acceptable acid addition salt thereof.

7. A compound of the formula

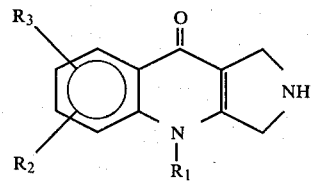

wherein
$R_1$ is hydrogen, alkyl of 1 to 4 carbon atoms, alkenyl or alkynyl, each 3 to 5 carbon atoms, the multiple bond of which is not adjacent to the nitrogen atom,
$R_2$ is chlorine or trifluoromethyl,
$R_3$ is hydrogen, fluorine, chlorine, bromine, hydroxyl, alkyl or alkoxy, each of 1 to 8 carbon atoms, in the form of the free base or in the form of a pharmaceutically acceptable acid addition salt thereof.

8. The compound of claim 6 wherein $R_1$ is H, $R_2$ is 7-OCH$_3$ and $R_3$ is H.

9. The compound of claim 6 wherein $R_1$ is CH$_3$, $R_2$ is 7-OCH$_3$ and $R_3$ is H.

10. The compound of claim 6 wherein $R_1$ is H, $R_2$ is 5-CH$_3$ and $R_3$ is H.

11. The compound of claim 6 wherein $R_1$ is H, $R_2$ is 5-F and $R_3$ is H.

12. The compound of claim 6 wherein $R_1$ is H, $R_2$ is 7-Cl and $R_3$ is H.

13. The compound of claim 6 wherein $R_1$ is H, $R_2$ is 5-CH$_3$ and $R_3$ is 7-Cl.

14. The compound of claim 6 wherein $R_1$ is H, $R_2$ is 5-CH$_3$ and $R_3$ is 7-CH$_3$.

15. The compound of claim 6 wherein $R_1$ is H, $R_2$ is 5-CH$_3$ and $R_3$ is 6-CH$_3$.

16. The compound of claim 6 wherein $R_1$ is H, $R_2$ is 7-$C_4H_9$ and $R_3$ is H.

17. The compound of claim 6 wherein $R_1$ is H, $R_2$ is 5-$C_3H_7O$ and $R_3$ is H.

18. The compound of claim 6 wherein $R_1$ is H, $R_2$ is 7-$C_6H_{13}O$ and $R_3$ is H.

19. The compound of claim 6 wherein $R_1$ is H, $R_2$ is 5-$CH_3O$ and $R_3$ is 8-$CH_3O$.

20. The compound of claim 6 wherein $R_1$ is $CH_2$-$CH=CH_2$, $R_2$ is 5-$CH_3$ and $R_3$ is 7-$CH_3$.

21. The compound of claim 6 wherein $R_1$ is H, $R_2$ is 5-$CH_3O$ and $R_3$ is 8-$CH_3$.

22. The compound of claim 6 wherein $R_1$ is H, $R_2$ is 6-$CF_3$ and $R_3$ is 7-Cl.

23. The compound of claim 6 wherein $R_1$ is H, $R_2$ is 5-Cl and $R_3$ is 7-Cl.

24. The compound of claim 6 wherein $R_1$ is H, $R_2$ is 7-$(CH_3)_2N$— and $R_3$ is H.

25. The compound of claim 6 wherein $R_1$ is H, $R_2$ is 7-OH and $R_3$ is H.

26. The compound of claim 6 wherein $R_1$ is $CH_3$, $R_2$ is 7-$NH_2$ and $R_3$ is H.

27. The compound of claim 6 wherein $R_1$ is —$(CH_2)_2C\equiv CH$, $R_2$ is 5-$C_3H_7$ and $R_3$ is 7-$C_2H_5$.

28. The compound of claim 6 wherein $R_1$ is $CH_3$, $R_2$ is 7-Br and $R_3$ is 5-$C_2H_5O$.

29. The compound of claim 6 wherein $R_1$ is $CH_3$, $R_2$ is 5-COOH and $R_3$ is H.

30. The compound of claim 6 wherein $R_1$ is H, $R_2$ is

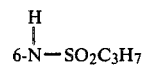

and $R_3$ is 5-$CH_3$.

31. The compound of claim 6 wherein $R_1$ is H, $R_3$ is

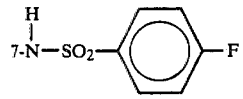

and $R_3$ is 5-$CH_3O$.

32. The compound of claim 6 wherein $R_1$ is $CH_3$, $R_2$ is 5-$C_4H_9O$ and $R_3$ is 7-F.

33. The compound of claim 6 wherein $R_1$ is $C_2H_5$, $R_2$ is 5-$C_7H_{15}$ and $R_3$ is 7-Br.

34. The compound of claim 6 wherein $R_1$ is $C_4H_9$, $R_2$ is 6-OH and $R_3$ is H.

35. The compound of claim 6 wherein $R_1$ is H, $R_2$ is

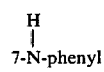

and $R_3$ is 5-$C_3H_7$.

36. The compound of claim 1 wherein $R_1$ is $C_2H_5$, $R_2$ is H and $R_3$ is H.

* * * * *

UNITED STATES PATENT AND TRADEMARK OFFICE
CERTIFICATE OF CORRECTION

PATENT NO. : 4,235,907
DATED : November 25, 1980
INVENTOR(S) : EMIL PFENNINGER

It is certified that error appears in the above—identified patent and that said Letters Patent is hereby corrected as shown below:

Column 3, line 65; before "Z," delete "cr" and substitute therefor --or--.

Column 10, Claim 7, line 45; after "each", insert --of--.

Column 10, Claim 7, line 47; after the comma, insert --and--.

Signed and Sealed this

Twenty-first Day of December 1982

[SEAL]

Attest:

*Attesting Officer*

GERALD J. MOSSINGHOFF

*Commissioner of Patents and Trademarks*